United States Patent
Isobe et al.

(10) Patent No.: US 8,429,973 B2
(45) Date of Patent: Apr. 30, 2013

(54) ULTRASONIC INSPECTION DEVICE AND ULTRASONIC INSPECTION METHOD

(75) Inventors: Hideo Isobe, Tokyo (JP); Ryoichi Arai, Yokohama (JP); Takahiro Ikeda, Yokosuka (JP); Noriyuki Yamane, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 419 days.

(21) Appl. No.: 12/750,181

(22) Filed: Mar. 30, 2010

(65) Prior Publication Data
US 2010/0251822 A1 Oct. 7, 2010

(30) Foreign Application Priority Data
Apr. 2, 2009 (JP) ................................ P2009-089757

(51) Int. Cl.
*G01N 29/06* (2006.01)
(52) U.S. Cl.
USPC ........................................................... 73/602
(58) Field of Classification Search ............. 73/602, 73/633, 634, 640
See application file for complete search history.

(56) References Cited

U.S. PATENT DOCUMENTS

| | | | | |
|---|---|---|---|---|
| 3,678,736 A | * | 7/1972 | May ............................... | 73/634 |
| 3,898,838 A | * | 8/1975 | Connelly ........................ | 73/634 |
| 3,978,714 A | * | 9/1976 | Shraiber et al. ................ | 73/625 |
| 5,214,616 A | * | 5/1993 | Terhune et al. ................. | 367/99 |
| 5,335,547 A | * | 8/1994 | Nakajima et al. .............. | 73/622 |
| 6,378,376 B1 | * | 4/2002 | Derman et al. ................. | 73/606 |
| 7,421,900 B2 | | 9/2008 | Karasawa et al. | |
| 7,496,456 B2 | * | 2/2009 | Hiyama et al. ................. | 702/39 |
| 2011/0000299 A1 | | 1/2011 | Isobe et al. | |

FOREIGN PATENT DOCUMENTS

| | | |
|---|---|---|
| EP | 1 462 799 A1 | 9/2004 |
| EP | 2 251 686 A1 | 11/2010 |
| JP | 63-309852 A | 12/1988 |
| JP | 2722087 B2 | 11/1997 |
| JP | 11-295276 A | 10/1999 |
| JP | 2004-053360 A | 2/2004 |
| JP | 2006-105657 A1 | 4/2006 |
| JP | 2009-204327 A | 9/2009 |

OTHER PUBLICATIONS

Translation of International Preliminary Report on Patentability of PCT/JP2010/002383, dated Nov. 24, 2011, 7 pages.

* cited by examiner

*Primary Examiner* — Peter Macchiarolo
*Assistant Examiner* — Rose M Miller
(74) *Attorney, Agent, or Firm* — Foley & Lardner LLP

(57) ABSTRACT

An ultrasonic transducer is provided with a distance measuring ultrasonic sensor for detecting a distance between the ultrasonic transducer and a surface of an inspection object and an inclination of the ultrasonic transducer with respect to the surface of the inspection object, to control the distance and the inclination of the ultrasonic transducer with respect to the inspection object based on information detected by the distance measuring ultrasonic sensor, and at least part of ultrasonic wave transmission/reception by the distance measuring ultrasonic sensor is performed during execution of aperture synthesis processing during which transmission/reception by the ultrasonic transducer is not performed.

5 Claims, 9 Drawing Sheets

(1) TRANSMISSION BAND OF DISTANCE MEASURING ULTRASONIC SENSOR (2) RECEPTION BAND OF DISTANCE MEASURING DEVICE (3) RECEPTION BAND OF FLAW DETECTOR

ULTRASONIC INSPECTION DEVICE AND ULTRASONIC INSPECTION METHOD

CROSS-REFERENCE TO THE INVENTION

This application is based upon and claims the benefit of priority from the prior Japanese Patent Application No. 2009-089757, filed on Apr. 2, 2009; the entire contents of which are incorporated herein by reference.

BACKGROUND OF THE INVENTION

1. Field of the Invention

The present invention relates to an ultrasonic inspection device and an ultrasonic inspection method visualizing a state of defect, void, and peeling of a joint portion and the like in a structure and a component, using ultrasonic waves transmitted/received by an ultrasonic transducer composed of a plurality of piezoelectric transducing parts which are arranged in a matrix or in a line and independently formed.

2. Description of the Related Art

In a conventional ultrasonic inspection device using an ultrasonic transducer composed of a plurality of piezoelectric transducing parts which are arranged in a matrix or in a line and independently formed, when the ultrasonic inspection device needs to automatically inspect an inspection object for flaws within a certain range, it is typical to provide a scanner mechanism which drives the ultrasonic transducer above the inspection object surface to scan the inspection object.

The scanner mechanism is composed using an orthogonal robot including axes such as an X-axis, a Y-axis, and a Z-axis, or an A-axis (a rotation axis around the X-axis), a B-axis (the rotation axis around the Y-axis), and a C-axis (the rotation axis around the Z-axis) as necessary, or an industrial robot mainly composed of an arm mechanism or the like.

The path of driving the ultrasonic transducer by the scanner mechanism needs to be created in advance based on the shape of the inspection object taking the aperture width of the ultrasonic transducer as one scan width. Methods of the creation include a method of creating the path in advance using computer software based on shape design data of the inspection object, and a method of actually driving the scanner mechanism and teaching and registering path information point by point. Further, a method of obtaining the actual shape of the inspection object by distance measurement by a distance sensor is also known (see, for example, JP-A 63-309852 (KOKAI)).

In an ultrasonic inspection, it is necessary that the ultrasonic wave emitted from the ultrasonic transducer enters the inspection object in a manner to be orthogonal to the surface thereof. Further, an ultrasonic inspection device performing flaw detection by the aperture synthesis method is also known (see, for example, JP-A 2004-53360 (KOKAI)), and it is important to keep the distance between the ultrasonic transducer and the inspection object surface constant in such an ultrasonic inspection device in which the flaw detection is performed by the aperture synthesis method. Note that there is a known technique which reduces mutual interference of ultrasonic waves using a plurality of ultrasonic probes having different frequencies to be able to inspect states of a plurality of joint portions at the same time see, for example, JP-A 11-295276 (KOKAI)).

Among the above-described conventional techniques, in the method of creating the path of driving the ultrasonic transducer in advance using the computer software based on shape design data, it is relatively easily possible to create the path information. However, the path information is based on the ideal shape design data, and therefore inconsistency may occur between the data and the actual shape of the inspection object, due to the working accuracy. Further, the inspect ion object is subjected to inspection while being fixed in the scanner mechanism, in which it is not easy to fix an inspection object in a complicated shape with high accuracy and high reproducibility.

Further, in the method of actually driving the scanner mechanism and teaching and registering path information point by point, a lot of time is required to teach and register path information point by point. Especially for a scanner mechanism having a complicated axis configuration, very complicated procedure and operation are necessary to teach and register path information, and therefore teaching and registering exact path information is a work accompanied by great difficulties. Further, even after obtaining shape data, there occurs inconsistency in path information unless the inspection object is accurately set in the scanner mechanism.

Further, also in the method of obtaining the actual shape by distance measurement by a distance sensor, unless the inspection object is accurately set in the scanner mechanism after obtaining the shape data, there occurs inconsistency in path information.

As described above, it has been difficult to create the path information which completely coincides with the state of the real inspection object.

To the above problem, there is a conceivable method that is capable of autonomously adjusting the error factor existing between the path information of the scanner mechanism and the real inspection object through use of a function of sensing the distance and the inclination between the ultrasonic transducer and the inspection object surface, and an actuator function of controlling the ultrasonic transducer.

Here, it is necessary to interpose a medium such as water or the like between the ultrasonic transducer and the inspection object in order for an ultrasonic wave to enter from the ultrasonic transducer to the inspection object or for the ultrasonic transducer to receive an ultrasonic echo from the inspection object. Under such circumstances, the ultrasonic inspection is often performed while the ultrasonic transducer and the inspection object are sunk in water. For the ultrasonic inspection in water, use of an ultrasonic probe as a sensor for detecting the distance or the inclination is conceivable as one method for integrating the function of sensing the distance or the inclination between the ultrasonic transducer and the inspection object surface, into the ultrasonic transducer. The ultrasonic probe that is usable in water and has an appropriate size condition and so on is selectable.

However, in the case where the ultrasonic probe is used as the sensor for detecting the distance or the inclination, interference of ultrasonic waves may occur between the detecting ultrasonic transducer and the ultrasonic probe for detecting the distance or the inclination because the ultrasonic probe uses the same ultrasonic wave as that of the ultrasonic transducer used for ultrasonic inspection. Occurrence of the interference of ultrasonic waves will deteriorate the inspection data and inspection image obtained via the ultrasonic transducer, or disable correct measurement of the distance and the inclination between the inspection object measured by the ultrasonic probe and the ultrasonic transducer.

Further, in the case where a plurality of ultrasonic probes are used for detecting the distance or the inclination, interference of ultrasonic waves may occur between the plural ultrasonic probes. Occurrence of such interference of ultrasonic waves will disable correct measurement of the distance and the inclination between the inspection object measured by the ultrasonic probes and the ultrasonic transducer.

The present invention has been made in consideration of the above-described circumstances in the prior art, and an object thereof is to provide an ultrasonic inspection device and an ultrasonic inspection method each capable of measuring the distance and the inclination between an ultrasonic transducer and an inspection object surface with high accuracy, and obtaining high-quality inspection data and inspection image.

SUMMARY OF THE INVENTION

An aspect of the ultrasonic inspection device of the present invention is an ultrasonic inspection device which drives a plurality of piezoelectric transducing parts constituting an ultrasonic transducer, the plural piezoelectric transducing parts being arranged in a matrix or in a line and independently formed, and performs aperture synthesis processing on electric signals generated by the plural piezoelectric transducing parts by receiving, from an inspection object, reflection echoes of ultrasonic waves emitted from the driven piezoelectric transducing parts, to synthesize a three-dimensional image of an inside of the inspection object, the ultrasonic inspection device including: a distance measuring ultrasonic sensor provided in the ultrasonic transducer, for detecting a distance between the ultrasonic transducer and a surface of the inspection object and an inclination of the ultrasonic transducer with respect to the surface of the inspection object, to control the distance and the inclination of the ultrasonic transducer with respect to the inspection object based on information detected by the distance measuring ultrasonic sensor, wherein at least part of ultrasonic wave transmission/reception by the distance measuring ultrasonic sensor is performed during execution of the aperture synthesis processing during which ultrasonic wave transmission/reception by the ultrasonic transducer is not performed.

Another aspect of the ultrasonic inspection device of the present invention is an ultrasonic inspection device which drives a plurality of piezoelectric transducing parts constituting an ultrasonic transducer, the plural piezoelectric transducing parts being arranged in a matrix or in a line and independently formed, and performs aperture synthesis processing on electric signals generated by the plural piezoelectric transducing parts by receiving, from an inspection object, reflection echoes of ultrasonic waves emitted from the driven piezoelectric transducing parts, to synthesize a three-dimensional image of an inside of the inspection object, the ultrasonic inspection device including: a distance measuring device which calculates a distance between the ultrasonic transducer and a surface of the inspection object and an inclination of the ultrasonic transducer with respect to the surface of the inspection object, from the electric signals by the ultrasonic transducer, to control the distance and the inclination of the ultrasonic transducer with respect to the inspection object based on calculation results by the distance measuring device.

An aspect of the ultrasonic inspection method of the present invention is an ultrasonic inspection method of driving a plurality of piezoelectric transducing parts constituting an ultrasonic transducer, the plural piezoelectric transducing parts being arranged in a matrix or in a line and independently formed, and performing aperture synthesis processing on electric signals generated by the plural piezoelectric transducing parts by receiving, from an inspection object, reflection echoes of ultrasonic waves emitted from the driven piezoelectric transducing parts, to synthesize a three-dimensional image of an inside of the inspection object, the ultrasonic inspection method including: providing a distance measuring ultrasonic sensor in the ultrasonic transducer, for detecting a distance between the ultrasonic transducer and a surface of the inspection object and an inclination of the ultrasonic transducer with respect to the surface of the inspection object, to control the distance and the inclination of the ultrasonic transducer with respect to the inspection object based on information detected by the distance measuring ultrasonic sensor; and performing at least part of ultrasonic wave transmission/reception by the distance measuring ultrasonic sensor during execution of the aperture synthesis processing during which ultrasonic wave transmission/reception by the ultrasonic transducer is not performed.

Another aspect of the ultrasonic inspection method of the present invention is an ultrasonic inspection method of driving a plurality of piezoelectric transducing parts constituting an ultrasonic transducer, the plural piezoelectric transducing parts being arranged in a matrix or in a line and independently formed, and performing aperture synthesis processing on electric signals generated by the plural piezoelectric transducing parts by receiving, from an inspection object, reflection echoes of ultrasonic waves emitted from the driven piezoelectric transducing parts, to synthesize a three-dimensional image of an inside of the inspection object, the ultrasonic inspection method including: calculating a distance between the ultrasonic transducer and a surface of the inspection object and an inclination of the ultrasonic transducer with respect to the surface of the inspection object, from the electric signals by the ultrasonic transducer, to control the distance and the inclination of the ultrasonic transducer with respect to the inspection object based on calculation results.

DETAILED DESCRIPTION OF THE INVENTION

Hereinafter, embodiments of an ultrasonic inspection device and an ultrasonic inspection method will be described in detail with reference to the drawings.

Figure 1:
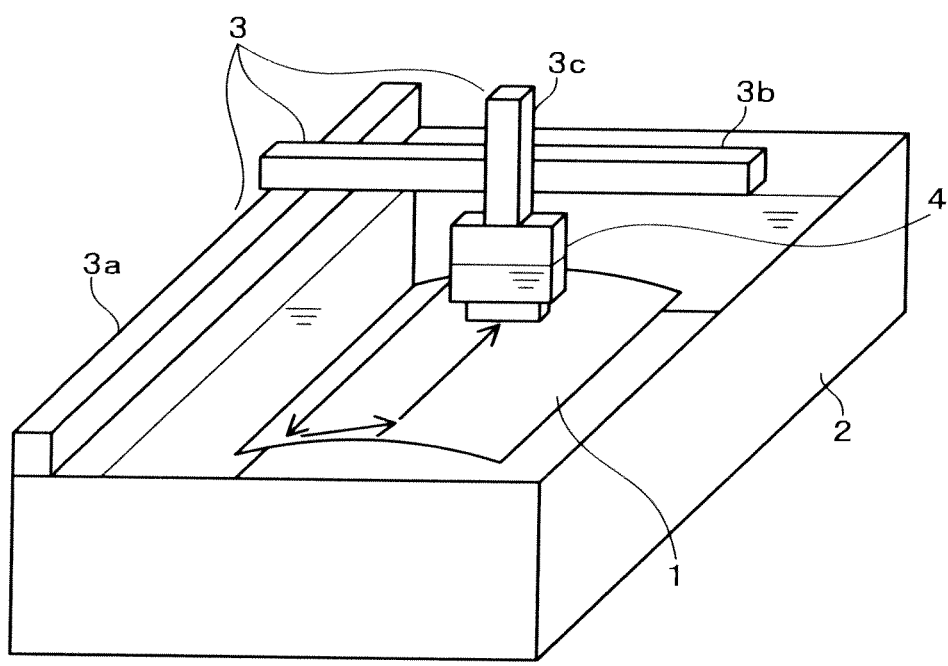
FIG. 1 is a perspective view showing a schematic configuration of the whole ultrasonic inspection device according to an embodiment of the present invention.

FIG. 1 is a perspective view schematically showing the outline of a configuration of a mechanical section of an ultrasonic inspection device according to an embodiment of the present invention. As shown in FIG. 1, the mechanical section of the ultrasonic inspection device is composed of a water tank 2 in which an inspection object 1 is set, a scanner mechanism 3, and an ultrasonic transducer 4 with a position detecting and controlling function fixed to a Z-shaft 3c of an X-shaft 3a, a Y-shaft 3b and the Z-shaft 3c constituting the scanner mechanism 3. The inspection object 1 is submerged in water in the water tank 2, and the ultrasonic transducer 4 with a position detecting and controlling function is also partially submerged in water.

(First Embodiment)

Figure 2:
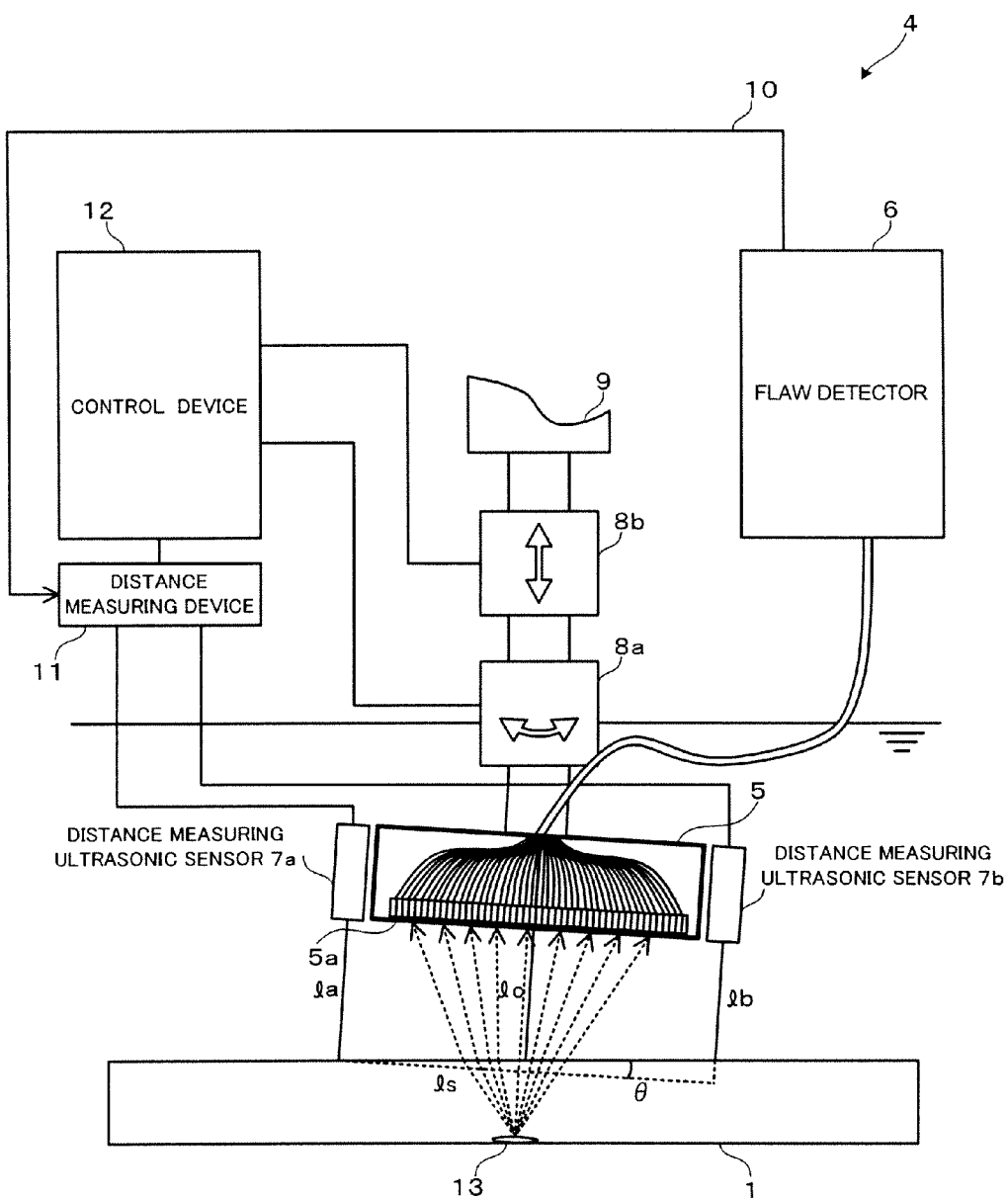
FIG. 2 is a block diagram showing a schematic configuration of a main part of an ultrasonic inspection device according to a first embodiment of the present invention.

FIG. 2 is a block diagram schematically showing a configuration of a main part of a first embodiment of the present invention, that is, the outline of the ultrasonic transducer 4 with a position detecting and controlling function shown in FIG. 1. FIG. 2 shows also a defect 13 inside the inspection object 1. The ultrasonic inspection device is for inspecting such an inspection object 1 for the defect 13 or the like therein.

As shown in FIG. 2, the ultrasonic transducer 4 with a position detecting and controlling function includes an ultrasonic transducer 5 composed of a plurality of piezoelectric transducing parts 5a arranged in a matrix or in a line and independently formed. The ultrasonic transducer 5 is electrically connected to a flaw detector 6. The flaw detector 6 drives the ultrasonic transducer 5 to emit ultrasonic waves, receives reflection echoes from the defect inside the inspection object 1 via the ultrasonic transducer 5, and performs imaging by the aperture synthesis processing.

Further, distance measuring ultrasonic sensors 7a and 7b are provided on both end portions of the ultrasonic transducer 5. To a top portion of the ultrasonic transducer 5, an inclination controlling actuator 8a is connected. The inclination controlling actuator 8a has a function of rotating the ultrasonic transducer 5 and the distance measuring ultrasonic sensors 7a and 7b around an axis vertical to FIG. 2 as shown by an arrow in the drawing. To a top portion of the inclination controlling actuator 8a, a distance controlling actuator 8b is connected. This distance controlling actuator 8b has a function of moving the ultrasonic transducer 5, the distance measuring ultrasonic sensors 7a and 7b, and the inclination controlling actuator 8a in a vertical direction as shown by an arrow in FIG. 2. The distance controlling actuator 8b is connected to the scanner mechanism 3 shown in FIG. 1 via a coupling part 9 with the scanner mechanism.

In the first embodiment, the ultrasonic transducer 4 with a position detecting and controlling function further includes a distance measuring device 11 and a control device 12. The distance measuring device 11 measures distances by driving the distance measuring ultrasonic sensors 7a and 7b in synchronization with a flaw detection signal 10 from the flaw detector 6 to transmit ultrasonic waves, and to receive reflection echoes from the surface of the inspection object 1 The control device 12 inputs the output of the distance measuring device 11. Using two distance measurement results by the distance measuring ultrasonic sensors 7a and 7b, the control device 12 controls the inclination controlling actuator 8a and the distance controlling actuator 8b so that the ultrasonic waves are perpendicular to the surface of the inspection object 1 and the distance between the inspection object 1 and the ultrasonic transducer 5 is fixed.

Though not shown in FIG. 2, the scanner mechanism 3 shown in FIG. 1 is provided on the coupling part 9. As described above, the scanner mechanism 3 has a function of integrally driving the ultrasonic transducer 5, the distance measuring ultrasonic sensors 7a and 7b, the inclination controlling actuator 8a, and the distance controlling actuator 8b to scan them above the inspection object 1.

As shown in FIG. 1, for performing ultrasonic inspection on the inspection object 1, it is necessary to create path information for inspection in advance. Using the path information, the scanner mechanism 3 drives the ultrasonic transducer 4 with a position detecting and controlling function, along the surface of the inspection object.

In the ultrasonic transducer 4 with a position detecting and controlling function, as shown in FIG. 2, the distance measuring ultrasonic sensors 7a and 7b are provided adjacent to the ultrasonic transducer 5 for flaw detection composed of the plural piezoelectric transducing parts 5a. The distance measuring ultrasonic sensors 7a and 7b transmit ultrasonic waves based on a command of the distance measuring device 11, which is in synchronization with the flaw detection signal 10 from the flaw detector 6. Then, the distance measuring device 11 receives the reflection echoes form the surface of the inspection object 1 via the distance measuring ultrasonic sensors 7a and 7b, and measures the time from the transmission to the reception of the ultrasonic waves to calculate the distances to the surface of the inspection object 1.

The two pieces of distance data between the inspection object 1 and the ultrasonic transducer 5 at both end portions thereof respectively measured by the distance measuring ultrasonic sensors 7a and 7b are transmitted from the distance measuring device 11 to the control device 12. The control device 12 calculates a distance 1c between a central portion of the ultrasonic transducer 5 and the inspection object 1 and an inclination θ of the ultrasonic transducer 5, using the pieces of distance data between the inspection object 1 and the ultrasonic transducer 5 at both end portions thereof measured by the distance measuring ultrasonic sensors 7a and 7b.

Assuming now that the distances respectively measured by the distance measuring ultrasonic sensors 7a and 7b are la and lb, and that the distance between the distance measuring ultrasonic sensors 7a and 7b is as shown in FIG. 2, the distance lc between the central portion of the ultrasonic transducer 5 and the inspection object 1 and the inclination θ of the ultrasonic transducer 5 are obtained, for example, by the following equations.

$$lc=(la+lb)/2$$

$$\theta=\tan^{-1}((la-lb)/ls)$$

Based on thus obtained distance and inclination data, the control device 12 controls the inclination controlling actuator 8a and the distance controlling actuator 8b. The control device 12 controls the distance between the ultrasonic transducer 5 and the surface of the inspection object 1 to be fixed. The control device controls the inclination of the ultrasonic transducer 5 so that the ultrasonic waves perpendicularly enters the inspection object 1. This makes it possible to perform accurate ultrasonic inspection even when there is an error in the path information for operating the scanner mechanism 3.

Figure 3:
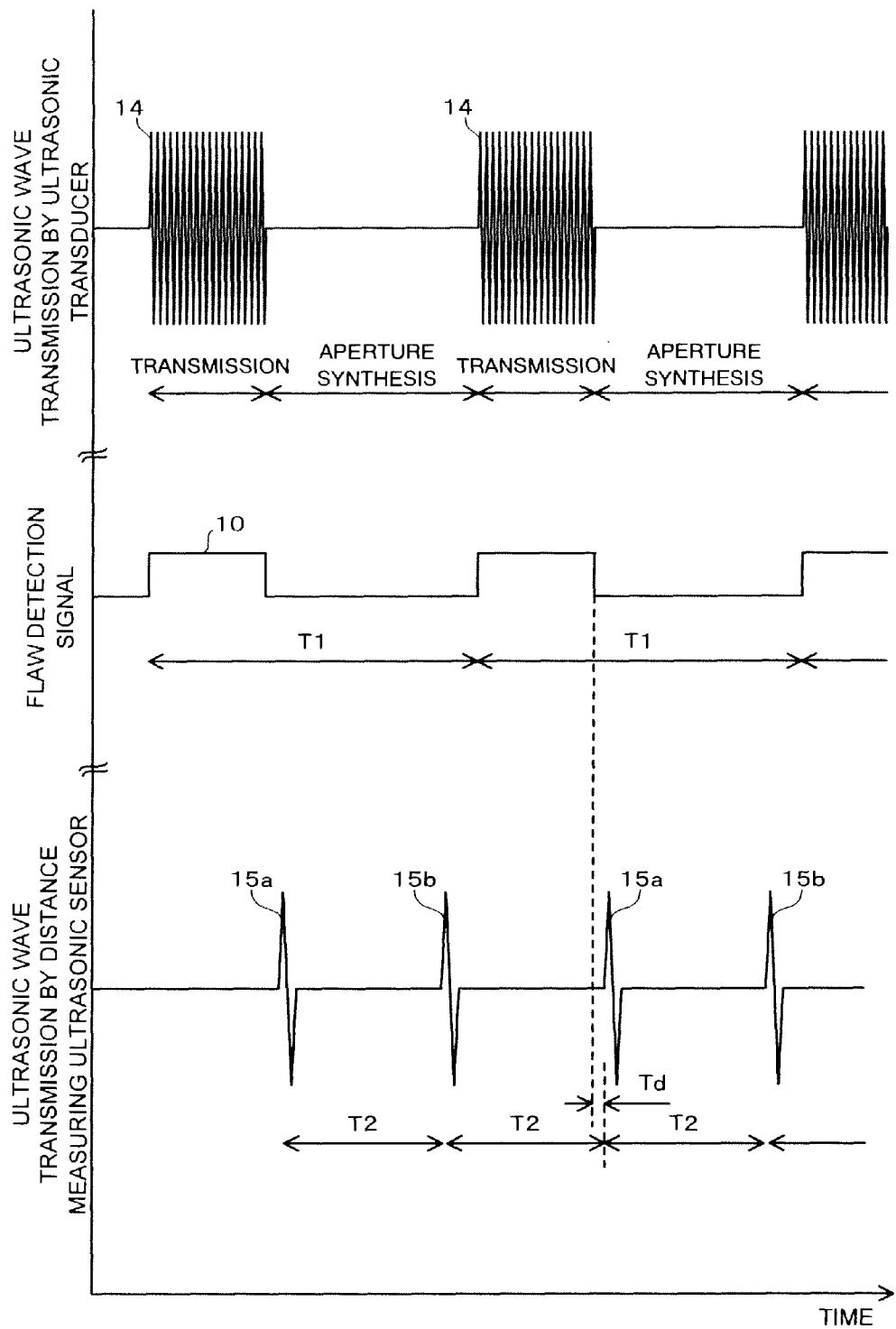
FIG. 3 is a diagram showing examples of ultrasonic wave transmission timings of the ultrasonic inspection device according to the first embodiment of the present invention.

FIG. 3 is a diagram showing ultrasonic wave transmission timings of the ultrasonic transducer 5 and the distance measuring ultrasonic sensors 7a and 7b in the above-described first embodiment. In FIG. 3, the horizontal axis is a common time axis, and waveforms shown at the upper section, the middle section, and the lower section are synchronized along the time axis.

In the first embodiment, a three-dimensional image of the inside of the inspection object is synthesized using the aperture synthesis method. In the aperture synthesis method, ultrasonic waves are sequentially generated from the plural piezoelectric transducing parts 5a of the ultrasonic transducer 5. The ultrasonic waves are reflected by the inspection object 1 as echoes. The reflection echoes are received by the plural piezoelectric transducing parts 5a to obtain echo waveforms corresponding to the number of combinations of transmission piezoelectric transducing parts and reception piezoelectric transducing parts (for example, in the case where there are 64 piezoelectric transducing parts 5a, 64×64=4096 echo waveforms). After that, aperture synthesis calculation (aperture synthesis processing) is performed using those echo waveforms to synthesize and obtain the image of the inside of the inspection object. Note as described in Patent Reference 2(JP-A 2004-53360 (KOKAI)), the aperture synthesis is proceded as follows. The region to be imaged is divided into meshes and times of reflection echoes reaching the regions divided into meshes are calculated in advance. Intensities of the reflection echoes at the regions divided into meshes are added to synthesize the three-dimensional image.

A flaw detection ultrasonic signal 14 of the ultrasonic transducer shown at the upper section in FIG. 3 indicates ultrasonic waves sequentially transmitted from the plural piezoelectric transducing parts 5a. The signal 14 is composed of waveforms corresponding to the number of combinations of the transmission piezoelectric transducing parts and the reception piezoelectric transducing parts. By repeating the sequence of performing the aperture synthesis calculation after the transmission, the inspection proceeds. During the aperture synthesis processing, the ultrasonic wave transmission/reception by the ultrasonic transducer 5 is not performed.

The waveform shown at the middle section in FIG. 3 shows an example of the flaw detection signal 10 outputted from the flaw detector 6 to the distance measuring device 11. In this example, the period of ultrasonic wave transmission by the ultrasonic transducer 5 is indicated by "1", and the period of non-transmission state is indicated by "0". One unit processing cycle time composed of the ultrasonic wave transmission by the ultrasonic transducer 5 and the aperture synthesis processing is T1.

The waveform shown at the lower section in FIG. 3 shows an example of the ultrasonic wave transmission timings of the distance measuring ultrasonic sensors 7a and 7b. During the time of the aperture synthesis, in synchronization with a trailing edge of the flaw detection signal 10, two ultrasonic waves are transmitted, namely, a distance measurement ultrasonic signal 15a is transmitted from the distance measuring ultrasonic sensor 7a and a distance measurement ultrasonic signal 15b is transmitted from the distance measuring ultrasonic sensor 7b. A transmission cycle T2 of the distance measuring ultrasonic sensors 7a and 7b is half T1. The distance measurement ultrasonic signal 15a is transmitted in synchronization with the trailing edge of the flaw detection signal 10 and with a fixed time delay Td. The distance measurement ultrasonic signal 15b is transmitted after a lapse of T2. This makes it possible to prevent the distance measurement ultrasonic signals 15a and 15b from interfering with the ultrasonic wave transmission by the ultrasonic transducer 5. As a result, distance measuring ultrasonic sensors 7a and 7b can be used without deteriorating the aperture synthesis image by the ultrasonic transducer 5.

Since there is no ultrasonic wave interference between the distance measuring ultrasonic sensor 7a and the distance measuring ultrasonic sensor 7b, and between the distance measuring ultrasonic sensors 7a and 7b and the ultrasonic transducer 5, accurate distance measurement is possible at all times. Further, the distance measurement ultrasonic signals 15a and 15b can be transmitted in a fixed cycle T2 (the transmission cycle of the same signal is T1=2×T2) at all times, so that the control by the control device 12 on the inclination controlling actuator 8a and the distance controlling actuator 8b can be stabilized and made accurate.

This makes it possible that the ultrasonic waves generated by driving the plural piezoelectric transducing parts 5a of the ultrasonic transducer 5 can be propagated with high accuracy through an acoustic propagation medium composed of liquid into the inspection object 1 which is composed of a layer with a planar or curved boundary and with a single acoustic characteristic or a plurality of acoustic characteristics, and the plural piezoelectric transducing parts 5a receive and piezoelectrically transduce the reflection echoes from the defect 13 and the like with a high positional accuracy. It causes to improve the accuracy of three-dimensional image synthesis of the inside of the inspection object 1 by the aperture synthesis, that is, the accuracy of imaging the defect 13.

(Second Embodiment)

Figure 4:
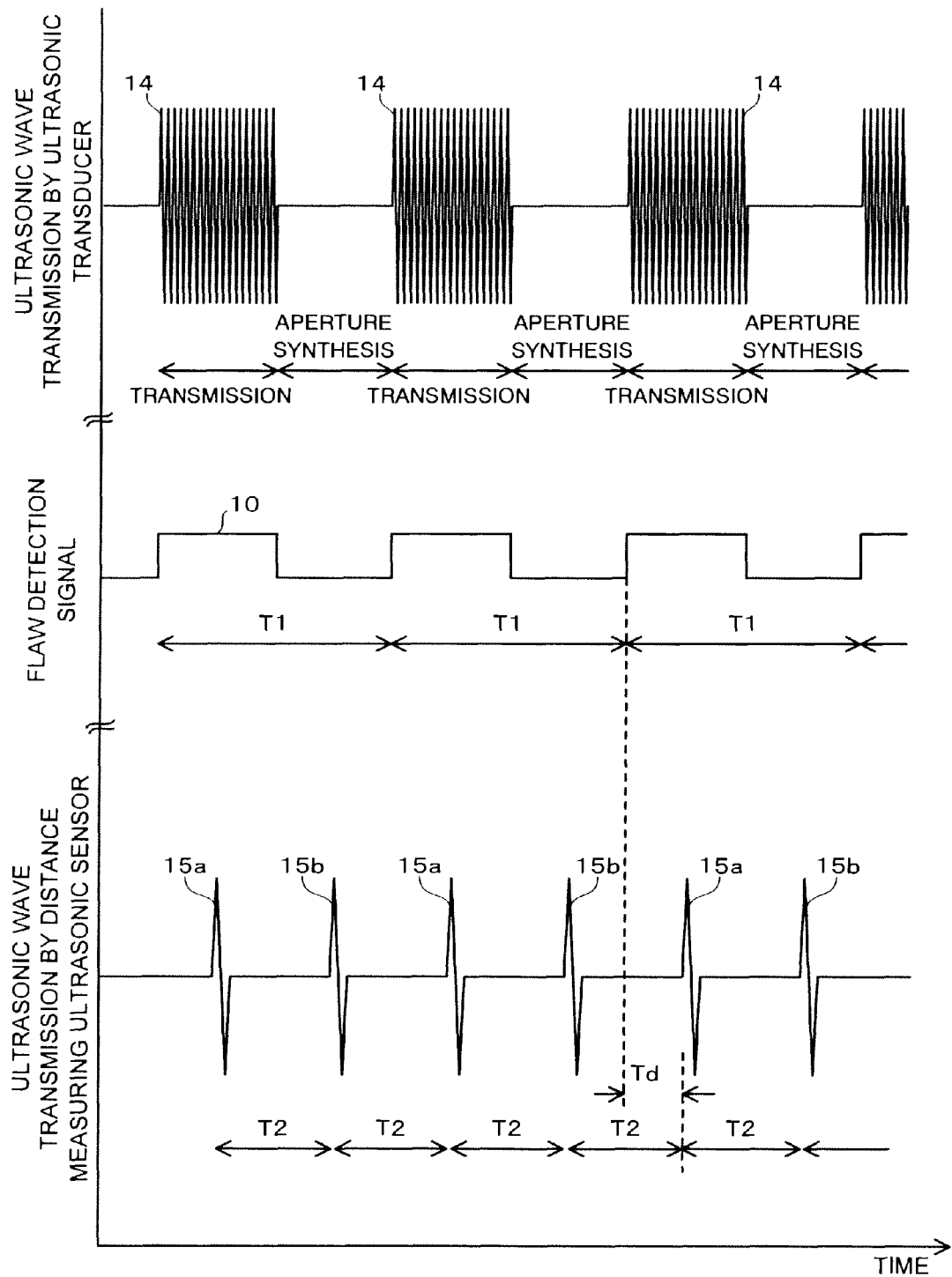
FIG. 4 is a diagram showing examples of ultrasonic wave transmission timings of an ultrasonic inspection device according to a second embodiment of the present invention.

FIG. 4 is a diagram showing ultrasonic wave transmission timings of an ultrasonic transducer 5 and distance measuring ultrasonic sensors 7a and 7b according to a second embodiment of the present invention. In FIG. 4, the horizontal axis is a common time axis, and waveforms shown at the upper section, the middle section, and the lower section are synchronized along the time axis.

In this second embodiment, the frequency band of the ultrasonic wave used by the distance measuring ultrasonic sensor 7a is different from that in the first embodiment. The other device configuration is the same as that of the first embodiment. The second embodiment is made to cope with the case in which the time of the aperture synthesis processing in one unit processing which is mainly composed of the ultrasonic wave transmission by the ultrasonic transducer 5 and the aperture synthesis processing is short.

In such a case, two distance measurement ultrasonic signals 15a and 15b cannot be transmitted in the aperture synthesis processing time, unlike the first embodiment, or even if possible, the transmission cycle is not fixed but extended as a whole, resulting in reduced distance measurement accuracy and control accuracy. To deal with this situation, the frequency band of the ultrasonic wave used by the distance measuring ultrasonic sensor 7a is made different from the frequency band of the ultrasonic wave used by the ultrasonic transducer 5. This enables transmission of the distance measurement ultrasonic signal 15a by the distance measuring ultrasonic sensor 7a also during the ultrasonic wave transmission by the ultrasonic transducer 5.

A flaw detection ultrasonic signal 14 of the ultrasonic transducer shown at the upper section in FIG. 4 shows ultrasonic waves sequentially transmitted from the plural piezoelectric transducing parts 5a. The signal 14 is composed of waveforms corresponding to the number of combinations of the transmission piezoelectric transducing parts and the reception piezoelectric transducing parts. By repeating the sequence of performing the aperture synthesis calculation after the transmission, the inspection proceeds. During the aperture synthesis processing, the ultrasonic wave transmission/reception by the ultrasonic transducer 5 is not performed. In this embodiment, the aperture synthesis processing time is relatively shorter than the transmission time of the flaw detection ultrasonic 14.

The waveform shown at the middle section in FIG. 4 shows an example of the flaw detection signal 10 outputted from the flaw detector 6 to the distance measuring device 11. In this example, the period of ultrasonic wave transmission by the ultrasonic transducer 5 is indicated by "1", and the period of non-transmission state is indicated by "0". One unit processing cycle time composed of the ultrasonic wave transmission by the ultrasonic transducer 5 and the aperture synthesis processing is T1.

The waveform shown at the lower section in FIG. 4 shows an example of the ultrasonic wave transmission timings of the distance measuring ultrasonic sensors 7a and 7b. The distance measurement ultrasonic signals 15a and 15b are transmitted in synchronization with a trailing edge of the flaw detection signal 10. A transmission cycle T2 of the distance measuring ultrasonic sensors 7a and 7b is half T1. The distance measurement ultrasonic signal 15a is transmitted in synchronization with the trailing edge of the flaw detection signal 10 and with a fixed time delay Td. The distance measurement ultrasonic signal 15b is transmitted after a lapse of time T2.

Though the distance measurement ultrasonic signal 15a is transmitted at the same timing as that of the ultrasonic wave transmission by the ultrasonic transducer 5, there is no interference because the frequency bands of the ultrasonic waves are different. The frequency band of the distance measuring ultrasonic sensor 7b may be the same as or different from that of the ultrasonic transducer 5 or the distance measuring ultrasonic sensor 7a. This makes it possible to transmit the distance measurement ultrasonic signals 15a and 15b in a sufficient cycle T2 (the transmission cycle of the same signal is T1=2×T2) not reducing the measurement accuracy even in the case where the aperture synthesis processing time is relatively short.

Figure 5:
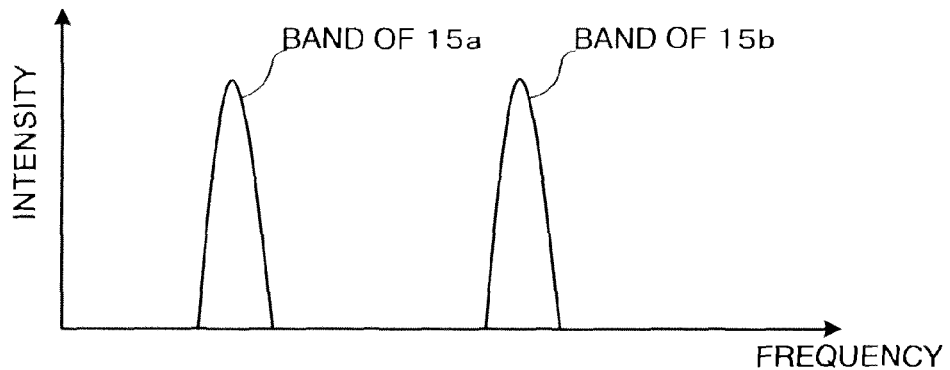
FIG. 5 is a graph showing examples of frequency bands of ultrasonic waves used in the second embodiment.
Figure 5:
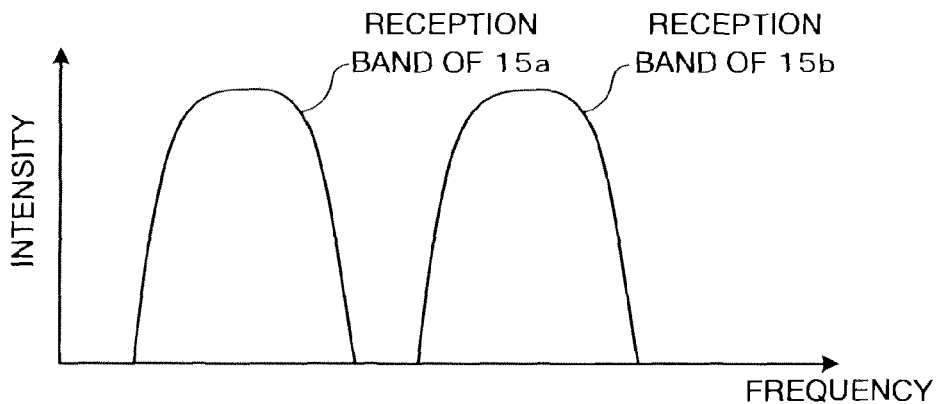
Figure 5:
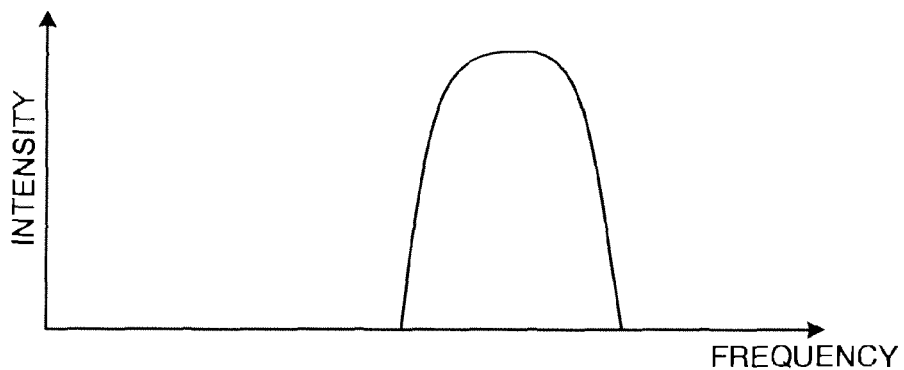

FIG. 5 is an explanatory graph of band examples of ultrasonic signals according to the second embodiment. In the band examples of the ultrasonic signals whose examples are shown in FIG. 5, the band of the distance measurement ultrasonic signal 15a is made to be lower than that of the distance measurement ultrasonic signal 15b, and frequency components of both of them are not overlapped with each other as shown at (1). Though not shown, the frequency band of the ultrasonic transducer 5 is the same as that of the distance measurement ultrasonic signal 15b. Further, as shown at (2) in FIG. 5, the reception band of the distance measuring device 11 is made different between the side for inputting the distance measurement ultrasonic signal 15a and the side for inputting the distance measurement ultrasonic signal 15b, in order to cope with the respective frequency bands. Thus, the ultrasonic signal emitted from the ultrasonic transducer 5 cannot be received on the side of the distance measuring device 11 for inputting the distance measurement ultrasonic signal 15a. Further, as shown at (3) in FIG. 5, the flaw detector 6 has a reception band to cope with the ultrasonic transducer 5, and thus cannot receive the distance measurement ultrasonic signal 15a.

In the second embodiment, it is possible as in the first embodiment to prevent the distance measurement ultrasonic signals 15a and 15b from interfering with the ultrasonic wave transmission by the ultrasonic transducer 5, and to use the distance measuring ultrasonic sensors 7a and 7b without deteriorating the aperture synthesis image by the ultrasonic transducer 5. Further, since there is no ultrasonic wave interference between the distance measuring ultrasonic sensor 7a and the distance measuring ultrasonic sensor 7h, and between the distance measuring ultrasonic sensors 7a and 7b and the ultrasonic transducer 5, accurate distance measurement is possible at all times. Further, the distance measurement ultrasonic signals 15a and 15b can be transmitted in a fixed cycle T2 (the transmission cycle of the same signal is T1=2×T2) at all times, so that the control by the control device 12 on the inclination controlling actuator 8a and the distance controlling actuator 8b can be stabilized and made accurate.

This makes it possible as in the first embodiment that the ultrasonic waves generated by driving the plural piezoelectric transducing parts 5a of the ultrasonic transducer 5 can be propagated with high accuracy through an acoustic propagation medium composed of liquid into the inspection object 1 which is composed of a layer with a planar or curved boundary and with a single acoustic characteristic or a plurality of acoustic characteristics, and the plural piezoelectric transducing parts 5a receive and piezoelectrically transduce the reflection echoes from the defect 13 and the like with a high positional accuracy. It causes to improve the accuracy of three-dimensional image synthesis of the inside of the inspection object 1 by the aperture synthesis, that is, the accuracy of imaging the defect 13. However, in the second embodiment, an ultrasonic sensor which can be used as the distance measuring ultrasonic sensor 7a is limited depending on the ultrasonic band used by the ultrasonic sensor, and a band-pass filter or the like needs to be provided in the distance measuring device 11 and the flaw detector 6 in order to receive the ultrasonic signal only in a specific frequency band.

(Third Embodiment)

Figure 6:
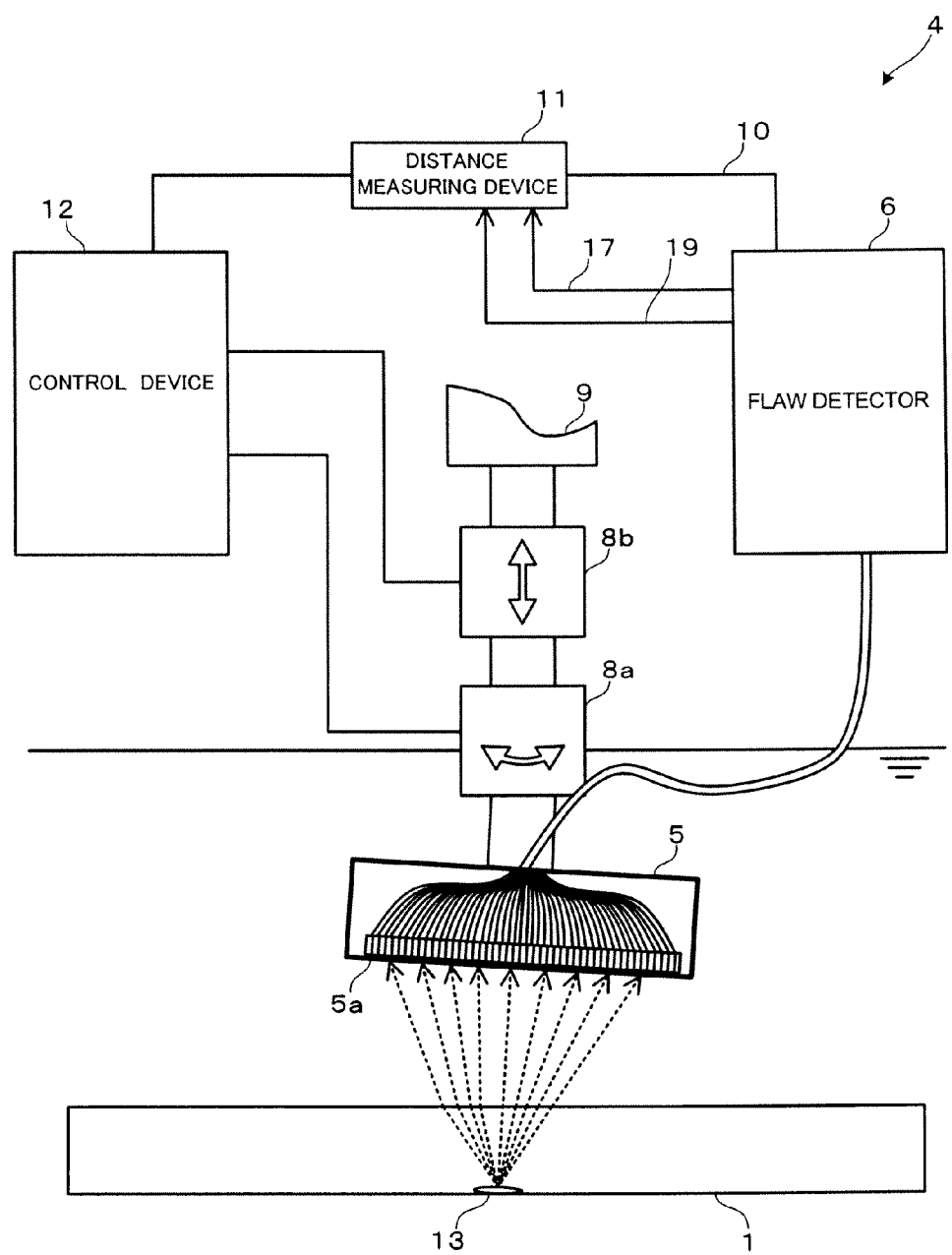
FIG. 6 is a block diagram showing a schematic configuration of a main part of an ultrasonic inspection device according to a third embodiment of the present invention.

FIG. 6 is a diagram schematically showing a main part of an ultrasonic inspection device according to a third embodiment of the present invention, that is, the outline of the ultrasonic transducer 4 with a position detecting and controlling function shown in FIG. 1. The ultrasonic inspection device is for inspecting such an inspection object 1 for the defect 13 or the like therein.

As shown in FIG. 6, the ultrasonic transducer 4 with a position detecting and controlling function includes an ultrasonic transducer 5 composed of a plurality of piezoelectric transducing parts 5a arranged in a matrix or in a line and independently formed. The ultrasonic transducer 5 is electrically connected to a flaw detector 6. The flaw detector 6 drives the ultrasonic transducer 5 to emit ultrasonic waves, receives reflection echoes from the defect or the like inside the inspection object 1 via the ultrasonic transducer 5, and performs imaging by the aperture synthesis processing.

In the third embodiment, no distance measuring ultrasonic sensors are provided on both end portions of the ultrasonic transducer 5. To a top portion of the ultrasonic transducer 5, an inclination controlling actuator 8a is connected. The inclination controlling actuator 8a has a function of rotating the ultrasonic transducer 5 around an axis vertical to FIG. 6 as shown by an arrow in the drawing. To a top portion of the inclination controlling actuator 8a, a distance controlling actuator 8b is connected. This distance controlling actuator 8b has a function of moving the ultrasonic transducer 5 and the inclination controlling actuator 8a in a vertical direction as shown by an arrow in FIG. 6, and is connected to the scanner mechanism 3 shown in FIG. 1 via a coupling part 9 with the scanner mechanism.

In this embodiment, the ultrasonic transducer 4 with a position detecting and controlling function further includes a distance measuring device 11 and a control device 12. The distance measuring device 11 is electrically connected to the flaw detector 6 so that a flaw detection signal 10 from the flaw detector 6 and ultrasonic signals (a drive signal line 17 and an echo signal line 19) which are transmitted/received by the ultrasonic flaw detector 6 using the ultrasonic transducer 5 are inputted into the distance measuring device 11. Thus, the ultrasonic transducer 5 can be used also for measuring the distance. The control device 12 inputs the output of the distance measuring device 11. Using the distance measurement result, the control device 12 controls the inclination controlling actuator 8a and the distance controlling actuator 8b so that the ultrasonic waves are perpendicular to the surface of the inspection object 1 and the distance between the inspection object 1 and the ultrasonic transducer 5 is fixed.

Though not shown in FIG. 6, the scanner mechanism 3 shown in FIG. 1 is provided on the coupling part 9. As described above, the scanner mechanism 3 has a function of integrally driving the ultrasonic transducer 5, the inclination controlling actuator 8a, and the distance controlling actuator 8b to scan them above the inspection object 1.

Figure 7:
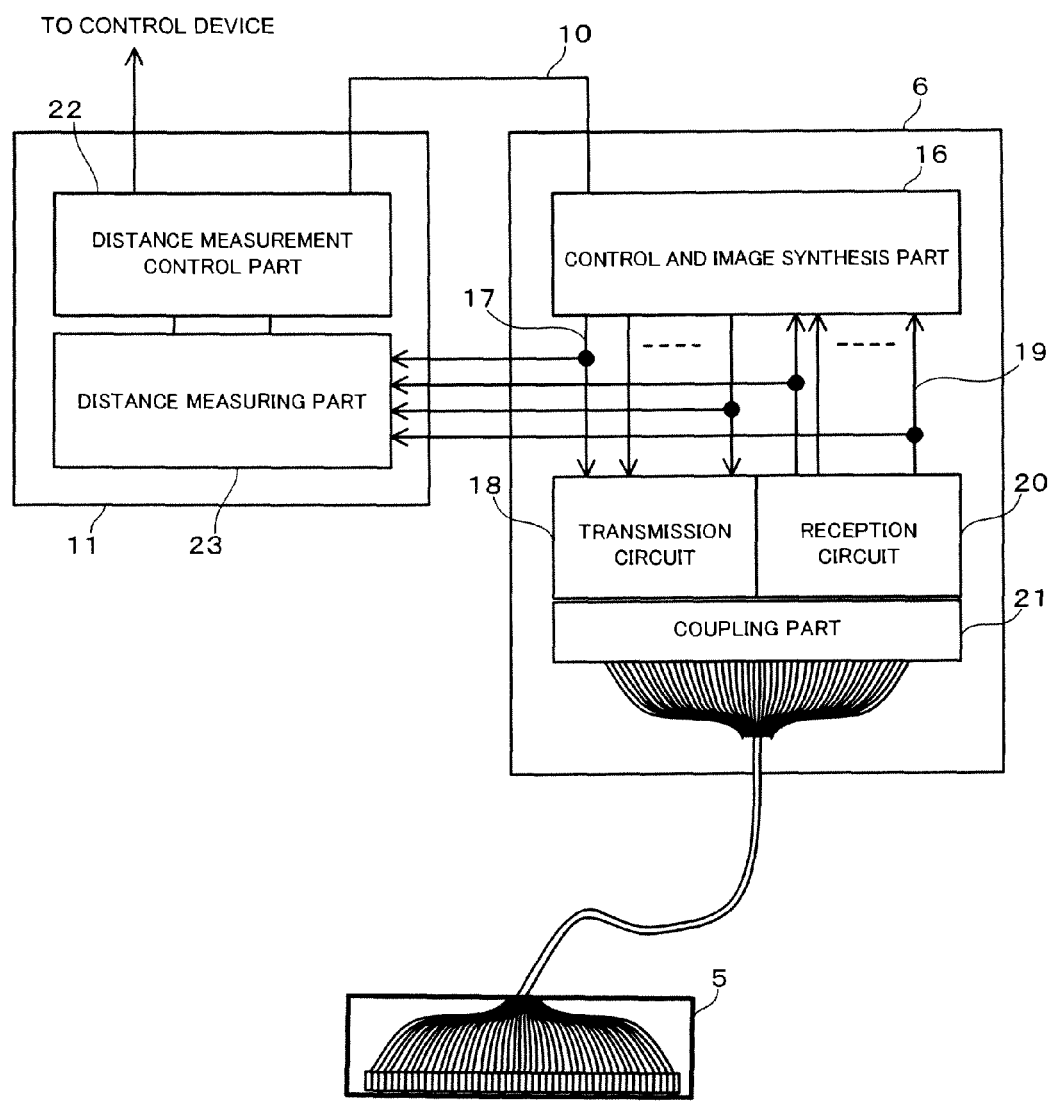
FIG. 7 is a block diagram showing a configuration of a flaw detector and a distance measuring device of the third embodiment of the present invention.

FIG. 7 is a block diagram showing a functional configuration of the flaw detector 6 and the distance measuring device 11 according to this embodiment. As shown in FIG. 7, the flaw detector 6 is composed of a control and image synthesis part 16, a drive signal line 17, a transmission circuit 18, an echo signal line 19, a reception circuit 20, and a coupling part 21.

The control and image synthesis part 16 control the whole flaw detector 6 to perform transmission processing and reception processing of ultrasonic waves and to image the inside of the inspection object 1 by the aperture synthesis processing based on the echo signals from the ultrasonic transducer 5. The drive signal line 17 is composed of a number of lines corresponding to the number of the piezoelectric transducing parts 5a of the ultrasonic transducer 5. The drive signal line 17 connects the control and image synthesis part 16 to the transmission circuit 18. The transmission circuit 18 is composed of a number of circuits corresponding to the number of the piezoelectric transducing parts 5a of the ultrasonic transducer 5. The transmission circuit 18 generates drive signals for the ultrasonic transducer 5.

The echo signal line 19 is composed of a number of lines corresponding to the number of the piezoelectric transducing parts 5a of the ultrasonic transducer 5. The echo signal line 19 connects the control and image synthesis part 16 to the reception circuit 20. The reception circuit 20 is composed of a number of circuits corresponding to the number of the piezoelectric transducing parts 5a of the ultrasonic transducer 5, and amplifies the echo signals received by the ultrasonic transducer 5. The coupling part 21 couples the output of the transmission circuit 18 to the input of the reception circuit 20, and is connected to the ultrasonic transducer 5.

The distance measuring device 11 is composed of a distance measurement control part 22 and a distance measuring part 23. The distance measurement control part 22 receives the flaw detection signal 10 from the flaw detector 6, and controls the whole distance measuring device 11 in synchronization therewith. The distance measuring part 23 inputs signals effective for distance measurement, for example, signals of piezoelectric transducing parts 5a corresponding to both end portions of the ultrasonic transducer 5, from the drive signal line 17 and the echo signal line 19 of the flaw detector 6. The distance measuring part 23 measures the time delay of the echo signals with respect to the drive signals to thereby measure the distances.

In the third embodiment having the above configuration, the distance measurement control part 22 detects the transmission/reception timings of the piezoelectric transducing part 5a used for distance measurement from the flaw detection signal 10, controls the distance measuring part 23 to measure the distance, and outputs the measurement result to the control device 12. This makes it possible that the drive signal and the echo signal of the ultrasonic transducer 5 used for imaging the inside of the inspection object 1 are used for distance measurement. It causes to eliminate the necessity to separately provide a sensor dedicated for distance measurement. Further, it becomes also unnecessary to consider the problem of interference when an ultrasonic probe is used as the distance measuring sensor.

This makes it possible as in the first embodiment that the ultrasonic waves generated by driving the plural piezoelectric transducing parts 5a of the ultrasonic transducer 5 can be propagated with high accuracy through an acoustic propagation medium composed of liquid into the inspection object 1 which is composed of a layer with a planar or curved boundary and with a single acoustic characteristic or a plurality of acoustic characteristics, and the plural piezoelectric transducing parts 5a receive and piezoelectrically transduce the reflection echoes from the defect 13 and the like with a high positional accuracy. It causes to improve the accuracy of three-dimensional image synthesis of the inside of the inspection object 1 by the aperture synthesis, that is, the accuracy of imaging the defect 13.

(Fourth Embodiment)

Figure 8:
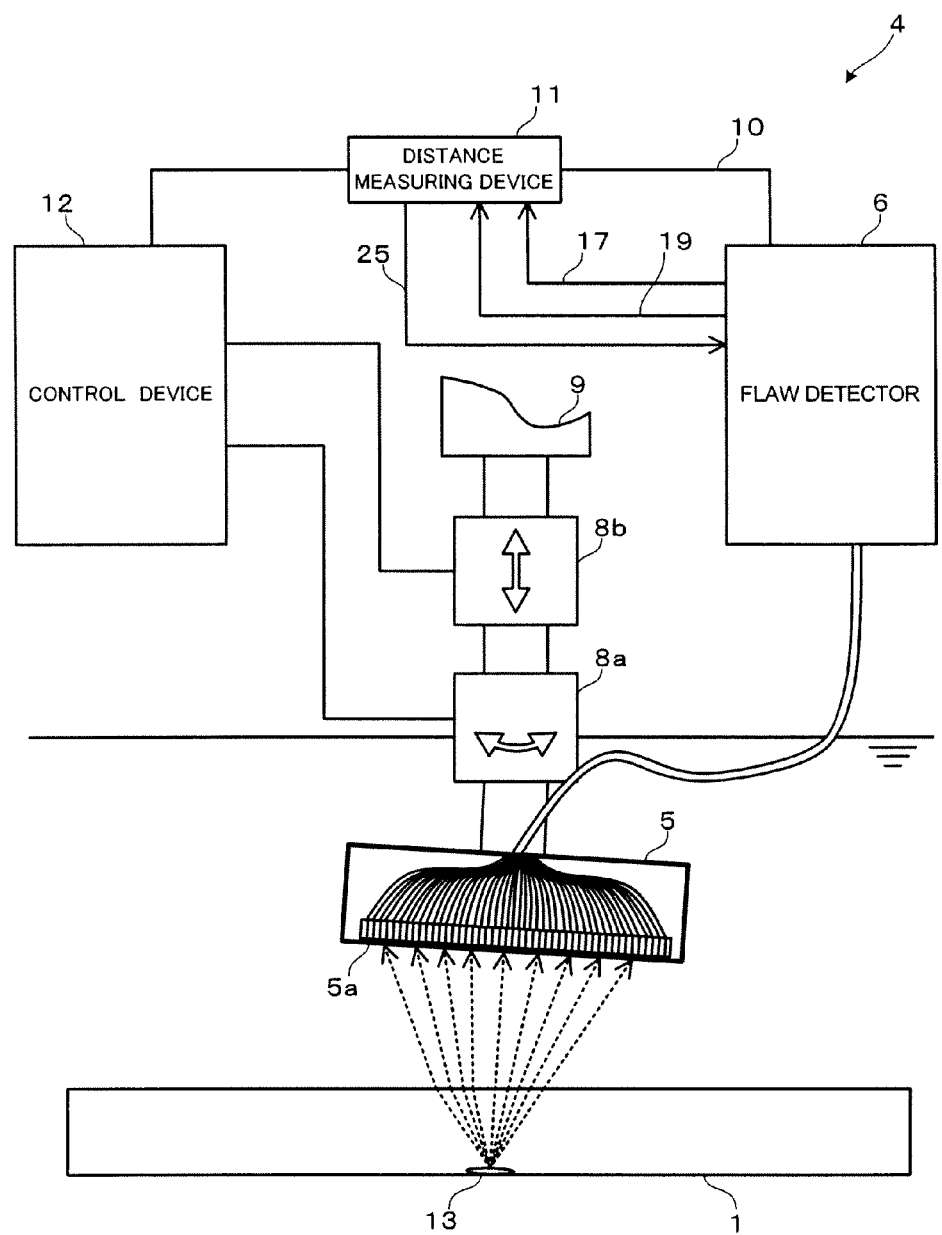
FIG. 8 is a block diagram showing a schematic configuration a main part of an ultrasonic inspection device according to a fourth embodiment of the present invention.

FIG. 8 is a diagram schematically showing a main part of an ultrasonic inspection device according to a fourth embodiment of the present invention, that is, the outline of the ultrasonic transducer 4 with a position detecting and controlling function shown in FIG. 1. In FIG. 8, in addition to taking of the ultrasonic signals (the drive signal line 17 and the echo signal line 19) between the flaw detector 6 and the distance measuring device 11 in FIG. 6, a distance measuring transducer drive signal line 25 is added. As a result, the ultrasonic transducer 5 is driven via the distance measuring transducer drive signal line 25 to perform distance measurement during the time when the ultrasonic transducer 5 is not performing ultrasonic wave transmission/reception for imaging the inspection object 1 (the aperture synthesis processing time).

Figure 9:
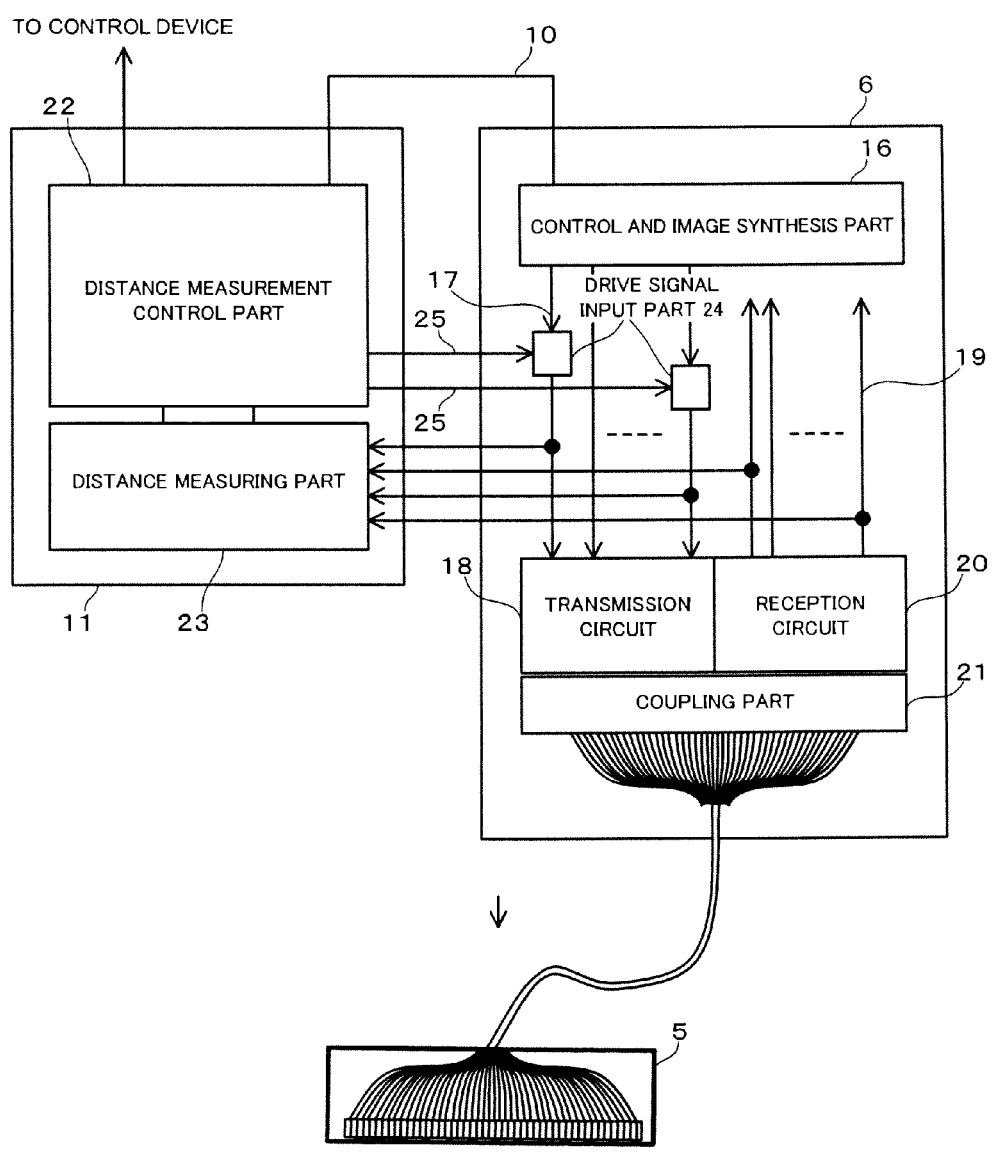
FIG. 9 is a block diagram showing a configuration of a flaw detector and a distance measuring device according to the fourth embodiment of the present invention.

FIG. 9 is a block diagram showing a functional configuration of the flaw detector 6 and the distance measuring device 11 in the fourth embodiment. In FIG. 9, drive signal input parts 24 are provided in the flaw detector 6 in addition to the configuration in FIG. 7, and distance measuring transducer drive signal lines 25 from the distance measurement control part 22 of the distance measuring device 11 are inputted to the drive signal input parts 24. The drive signal input part 24 has a function of transmitting drive commands to the transmission circuit 18. The drive commands includes a drive command on the drive signal line 17 from the control and image synthesis part 16 and a drive command on the distance measuring transducer drive signal line 25 from the distance measurement control part 22 of the distance measuring device 11.

In the fourth embodiment having the above configuration, the distance measuring device 11 can independently drive the ultrasonic transducer 5 to measure the distance or the inclination. The timing when the distance measuring device 11 drives the ultrasonic transducer 5 to measure the distance is the time when the ultrasonic transducer 5 is not performing ultrasonic wave transmission/reception for imaging the inspection object 1 (the aperture synthesis processing time), and is the same as the transmission timing of the distance measurement ultrasonic signal 15b in the description for FIG. 4.

According to the ultrasonic inspection device of the fourth embodiment, both of the distance measurement using the flaw detection ultrasonic signal 14 of the ultrasonic transducer 5 and the distance measurement at the timing of the aperture synthesis processing become possible without providing an independent distance measuring sensor. Further, the problem of interference of ultrasonic waves does not occur. This makes it possible to substantially eliminate the constraint relating to the transmission of the distance measurement ultrasonic wave, and to measure the distance in a fixed cycle at all times and in a sufficient cycle not reducing the measurement accuracy.

This makes it possible that the ultrasonic waves generated by driving the plural piezoelectric transducing parts 5a of the ultrasonic transducer 5 can be propagated with high accuracy through an acoustic propagation medium composed of liquid into the inspection object 1 which is composed of a layer with a planar or curved boundary and with a single acoustic characteristic or a plurality of acoustic characteristics, and the plural piezoelectric transducing parts 5a receive and piezoelectrically transduce the reflection echoes from the defect 13 and the like with a high positional accuracy. It causes to improve the accuracy of three-dimensional image synthesis of the inside of the inspection object 1 by the aperture synthesis processing, that is, the accuracy of imaging the defect 13.

As described above, in the embodiments using the ultrasonic probe as the sensor detecting the distance between the ultrasonic transducer and the inspection object surface or the inclination of the ultrasonic transducer with respect to the inspection object surface, it becomes possible to prevent interference between the ultrasonic wave emitted from the ultrasonic transducer and the ultrasonic wave detecting the distance or the inclination, and to measure the distance or the inclination in a fixed cycle at all times. This makes it possible to control the distance and the inclination of the ultrasonic transducer with respect to the inspection object surface with high accuracy, and to perform accurate ultrasonic inspection.

The present invention is not limited to the above-described embodiments, but may be variously changed. Further, the embodiments of the present invention can be expanded and modified within the technical scope of the present invention. The expanded and modified embodiments are also included in the technical scope of the present invention.

What is claimed is:

1. An ultrasonic inspection device, comprising:
   a plurality of piezoelectric transducing parts constituting an ultrasonic transducer, the plural piezoelectric transducing parts being arranged in a matrix or in a line;
   a flaw detector configured to perform aperture synthesis processing by adding reflection waveforms of ultrasonic waves which are emitted from the piezoelectric transducing parts and are reflected by an inspection object, to synthesize a three-dimensional image of an inside of the inspection object; and
   a distance measuring device configured to calculate a distance between the ultrasonic transducer and a surface of the inspection object and an inclination of the ultrasonic transducer with respect to the surface of the inspection object, from a detection signal by a distance measuring ultrasonic sensor, to control the distance and the inclination of the ultrasonic transducer with respect to the inspection object based on calculation results by the distance measuring device,
   wherein at least part of ultrasonic wave transmission/reception by the distance measuring ultrasonic sensor is performed during execution of the aperture synthesis processing during which ultrasonic wave transmission/reception by the ultrasonic transducer is not performed.

2. The ultrasonic inspection device according to claim 1,
   wherein a plurality of the distance measuring ultrasonic sensors are provided in the ultrasonic transducer;
   wherein at least one of the plural distance measuring ultrasonic sensors is a distance measuring ultrasonic sensor with a different frequency band which transmits/receives ultrasonic waves in a frequency band different from a frequency band of the ultrasonic transducer; and
   wherein the ultrasonic wave transmission/reception by the distance measuring ultrasonic sensor with a different frequency band is performed during the ultrasonic wave transmission/reception by the ultrasonic transducer.

3. The ultrasonic inspection device according to claim 1,
   wherein the piezoelectric transducing parts at both end portions of the ultrasonic transducer are used as the distance measuring ultrasonic sensors; and
   wherein during the execution of aperture synthesis processing, the distance measuring device drives the ultrasonic transducer to obtain the detection signals indicating the distance between the ultrasonic transducer and the surface of the inspection object and the inclination of the ultrasonic transducer with respect to the surface of the inspection object, and calculates the distance and the inclination by the obtained detection signals.

4. An ultrasonic inspection device, comprising:
   a plurality of piezoelectric transducing parts constituting an ultrasonic transducer, the plural piezoelectric transducing parts being arranged in a matrix or in a line;
   a flaw detector configured to perform aperture synthesis processing by adding reflection waveforms of ultrasonic waves which are emitted from the piezoelectric transducing parts and are reflected by an inspection object, to synthesize a three-dimensional image of an inside of the inspection object; and
   a distance measuring device configured to calculate a distance between the ultrasonic transducer and a surface of the inspection object and an inclination of the ultrasonic transducer with respect to the surface of the inspection object, from the electric signals by the ultrasonic transducer, to control the distance and the inclination of the ultrasonic transducer with respect to the inspection object based on calculation results by the distance measuring device,
   wherein when the ultrasonic transducer is performing ultrasonic wave transmission/reception for inspection, the distance measuring device calculates the distance and the inclination using electric signals thereof; and
   wherein when the ultrasonic transducer is not performing ultrasonic wave transmission/reception for inspection, the distance measuring device drives the ultrasonic transducer to obtain electric signals, and calculates the distance and the inclination using the obtained electric signals.

5. An ultrasonic inspection method of driving a plurality of piezoelectric transducing parts constituting an ultrasonic transducer, the plural piezoelectric transducing parts being arranged in a matrix or in a line and independently formed, and
   performing aperture synthesis processing on electric signals generated by the plural piezoelectric transducing parts by receiving, from an inspection object, reflection echoes of ultrasonic waves emitted from the driven piezoelectric transducing parts, to synthesize a three-dimensional image of an inside of the inspection object,
   the ultrasonic inspection method comprising:
   providing a distance measuring device which calculates a distance between the ultrasonic transducer and a surface of the inspection object and an inclination of the ultrasonic transducer with respect to the surface of the inspection object, from a detection signal by a distance measuring ultrasonic sensor, to control the distance and the inclination of the ultrasonic transducer with respect to the inspection object based on calculation results by the distance measuring device; and
   performing at least part of ultrasonic wave transmission/reception by the distance measuring ultrasonic sensor during execution of the aperture synthesis processing during which ultrasonic wave transmission/reception by the ultrasonic transducer is not performed.

\* \* \* \* \*